[19] United States Patent
Wrenn et al.

[11] Patent Number: 6,123,666
[45] Date of Patent: *Sep. 26, 2000

[54] LARYNGOSCOPE BLADE WITH FIBEROPTIC SCOPE FOR REMOTE VIEWING AND METHOD FOR TEACHING THE PROPER INSERTION OF A LARYNGOSCOPE BLADE INTO THE AIRWAY OF A PATIENT

[75] Inventors: Keith D. Wrenn, Brentwood; Steven J. White, Nashville, both of Tenn.

[73] Assignee: Vanderbilt University, Nashville, Tenn.

[*] Notice: This patent issued on a continued prosecution application filed under 37 CFR 1.53(d), and is subject to the twenty year patent term provisions of 35 U.S.C. 154(a)(2).

[21] Appl. No.: 09/069,602

[22] Filed: Apr. 29, 1998

[51] Int. Cl.⁷ .............................. A61B 1/267; G09B 23/28
[52] U.S. Cl. ........................... 600/188; 600/190; 434/262
[58] Field of Search .................................. 434/262, 265; 600/185, 188, 190, 199, 120

[56] References Cited

U.S. PATENT DOCUMENTS

| | | | |
|---|---|---|---|
| 4,086,919 | 5/1978 | Bullard | 600/188 |
| 4,484,896 | 11/1984 | Kohnke | 434/265 |
| 5,263,472 | 11/1993 | Ough | 600/188 |
| 5,363,838 | 11/1994 | George | 600/188 X |
| 5,381,787 | 1/1995 | Bullard | 600/196 X |
| 5,529,570 | 6/1996 | Storz | 600/185 X |
| 5,603,688 | 2/1997 | Upsher | 600/190 |
| 5,701,904 | 12/1997 | Simmons et al. | 600/559 X |
| 5,800,344 | 9/1998 | Wood, Sr. et al. | 600/188 |
| 5,827,178 | 10/1998 | Berall | 600/185 |
| 5,846,186 | 12/1998 | Upsher | 600/185 |

FOREIGN PATENT DOCUMENTS

| | | | |
|---|---|---|---|
| 2825376 | 12/1978 | Germany | 434/262 |
| 91012044 | 8/1991 | WIPO | 600/120 |

Primary Examiner—Jeffrey A. Smith
Attorney, Agent, or Firm—Waddey & Patterson; Mark J. Patterson

[57] ABSTRACT

A laryngoscope equipped with a fiberoptic scope for enabling simultaneous remote observation of the airway and associated structures during insertion of the laryngoscope blade. The laryngoscope includes a blade member configured for attachment to a handle, a conduit positioned adjacent the blade member for housing a fiberoptic scope. The fiberoptic scope includes fibers for illuminating an area adjacent a distal end of the blade and viewing fibers for transmitting a visual image of the illuminated area to a remote viewing system. A clear cap is provided for the end of the conduit to protect the fiberoptic scope from patient secretions.

13 Claims, 3 Drawing Sheets

LARYNGOSCOPE BLADE WITH FIBEROPTIC SCOPE FOR REMOTE VIEWING AND METHOD FOR TEACHING THE PROPER INSERTION OF A LARYNGOSCOPE BLADE INTO THE AIRWAY OF A PATIENT

BACKGROUND OF THE INVENTION

The present invention relates generally to laryngoscopes, and more particularly to laryngoscope blades having an integral fiber optic scope electrically connected to a remote viewing system for enabling an instructor to observe and direct the insertion of the laryngoscope by a student.

Endotracheal intubation is a life-saving procedure that must be mastered by many medical disciplines. Typically, the intubator inserts a laryngoscope blade attached to a handle into a patient's mouth to displace the tongue and to visualize the epiglottis and larynx in order to insert an endotracheal tube. Illumination of the structures in the airway is provided by a light source at the tip of the blade. The light source is generally powered by a battery source contained in the handle.

Because intubation is frequently performed in emergency situations, it is critical that a physician or healthcare professional be trained to properly insert a laryngoscope. Malposition of the laryngoscope blade and prolonged intubation attempts pose risks to the patient and may prevent the prompt and effective administration of treatment. Unfortunately, in teaching the mechanics of intubation, an instructor is precluded from viewing the anatomy while a student is performing the intubation procedure. Thus, the instructor is unable to provide necessary instruction and feedback to the student to facilitate proper insertion and placement of the laryngoscope blade.

Accordingly, it will be appreciated by those skilled in the art that it is convenient and desirable to have a laryngoscope equipped with means for illuminating and remotely viewing the pharynx, larynx, trachea and associated structures during intubation of a patient. To this end, there have been several attempts to devise laryngoscopes which include ruminating devices.

One such attempt was disclosed in U.S. Pat. No. 5,363,838, issued to George, which is directed to an intubating scope with an auxiliary fiber optic camera connected to an external electronic viewing screen. The intubating scope is disposed within an endotracheal tube, which is inserted into the airway after a laryngoscope blade has been inserted and used to open the airway. Accordingly, the fiber optic scope is useful for guiding the endotracheal tube further into the larynx and trachea after a laryngoscope has been inserted and utilized to open the airway. However, the device is not useful for teaching the basic skill of properly inserting the laryngoscope blade in order to facilitate the subsequent placement of an endotracheal tube.

U.S. Pat. No. 4,901,708, issued to Lee, discloses a viewing laryngoscope comprising a blade having a pair of fiberoptic bundles. One bundle transmits light to the distal end of the blade, and the other bundle is optically coupled to a lens for line-of-sight viewing of the area adjacent the distal end of the blade. While the device enables line-of-sight viewing by the user, it does not enable remote simultaneous viewing of the airway during insertion of the blade for facilitating instruction regarding proper placement of an endotracheal tube.

U.S. Pat. No. 5,261,392, issued to Wu, discloses a laryngoscope comprising a blade and an integral handle having an enclosed cavity which receives a fiberoptic bundle having illuminating and viewing fibers. An eyepiece is connected to view the image from the viewing fiberoptic bundle.

U.S. Pat. No. 5,355,870, issued to Lacy, discloses a laryngoscope having a removable blade assembly containing a light-conducting rod which delivers illumination distally from a light source in the handle. However, the Lacy device does not enable remote simultaneous viewing during intubation.

U.S. Pat. No. 4,306,547, issued to Lowell, discloses a rigid fiberoptic laryngoscope having a forwardly extending blade and an instrument supporting channel. The laryngoscope includes a viewing assembly and light source each connected to fiberoptic bundles.

Another device used as a teaching aid in intubation is an "airway cam", which includes a headgear-mounted microcamera that transmits what is observed by a student while carrying out an intubation procedure. With this device, the visibility is limited to only what the student is able to observe because the camera is not inserted into the airway during intubation. Further, the airway cam requires a separate piece of equipment to enable remote viewing.

All of the aforementioned devices include light means for illuminating the air passage during insertion of an endotracheal tube. However, none of the devices enables simultaneous remote viewing during the initial placement and positioning of the laryngoscope blade to open the airway for insertion of the endotracheal tube. What is needed then, is a larygoscope blade equipped with means for illuminating the air passage and for enabling remote viewing of the airway during insertion of the blade. In this manner, an instructor can simultaneously observe the anatomy of the patient via a remote viewing system during intubation by a student to insure proper insertion of the laryngoscope blade.

SUMMARY OF THE INVENTION

The present invention comprises a laryngoscope including a handle portion and a blade equipped with a fiberoptic scope that is configured to enable simultaneous remote observation of the pharynx, larynx, trachea and associated structures during intubation to facilitate instruction as to the proper placement or positioning of the laryngoscope blade prior to insertion of an endotracheal tube.

The laryngoscope blade includes an elongated blade member extending from a base. The blade comprises a plate portion and a flange extending perpendicularly from an upper edge of the plate portion. The flange extends beyond the length of the plate portion and terminates in a rounded tip. A lip extends perpendicularly from a lower edge of the plate portion and is substantially parallel to the flange.

A conduit for housing a fiberoptic scope extends along an outer side of the plate portion of the blade member, passes through an opening formed in the plate portion and extends along an inner side of the plate portion to a distal end thereof.

The fiberoptic scope is insertable into the conduit and illuminates the area adjacent the end of the blade. The fiberoptic scope is operably connected to a remote viewing system, including a monitor for enabling simultaneous remote viewing of the airway during insertion of the laryngoscope blade. One advantage of the present system is that the fiberoptic scope may be removed from the conduit and used for other diagnostic purposes, such as examination of the larynx, bronchi and nasopharyn, when not being used in conjunction with the laryngoscope blade to teach and/or supervise intubation procedures.

It is an object of the present invention to provide a laryngoscope that is useful for instructing students in the proper placement and positioning of a laryngoscope blade during intubation procedures.

It is another object of the present invention to provide a laryngoscope equipped with a fiberoptic scope for enabling simultaneous remote viewing of the airway during insertion of the laryngoscope blade.

It is another object of the present invention to provide a laryngoscope having a blade equipped with a conduit for housing a fiberoptic scope that illuminates an area adjacent the distal end of the blade and that transmits a visual image of the illuminated area to a remote viewing system.

These and other objects, features and advantages shall become apparent after consideration of the description and drawings set forth herein. All such objects, features and advantages are contemplated to be within the scope of the present invention even though not specifically set forth herein.

DESCRIPTION OF THE PREFERRED EMBODIMENT

Figure 1:
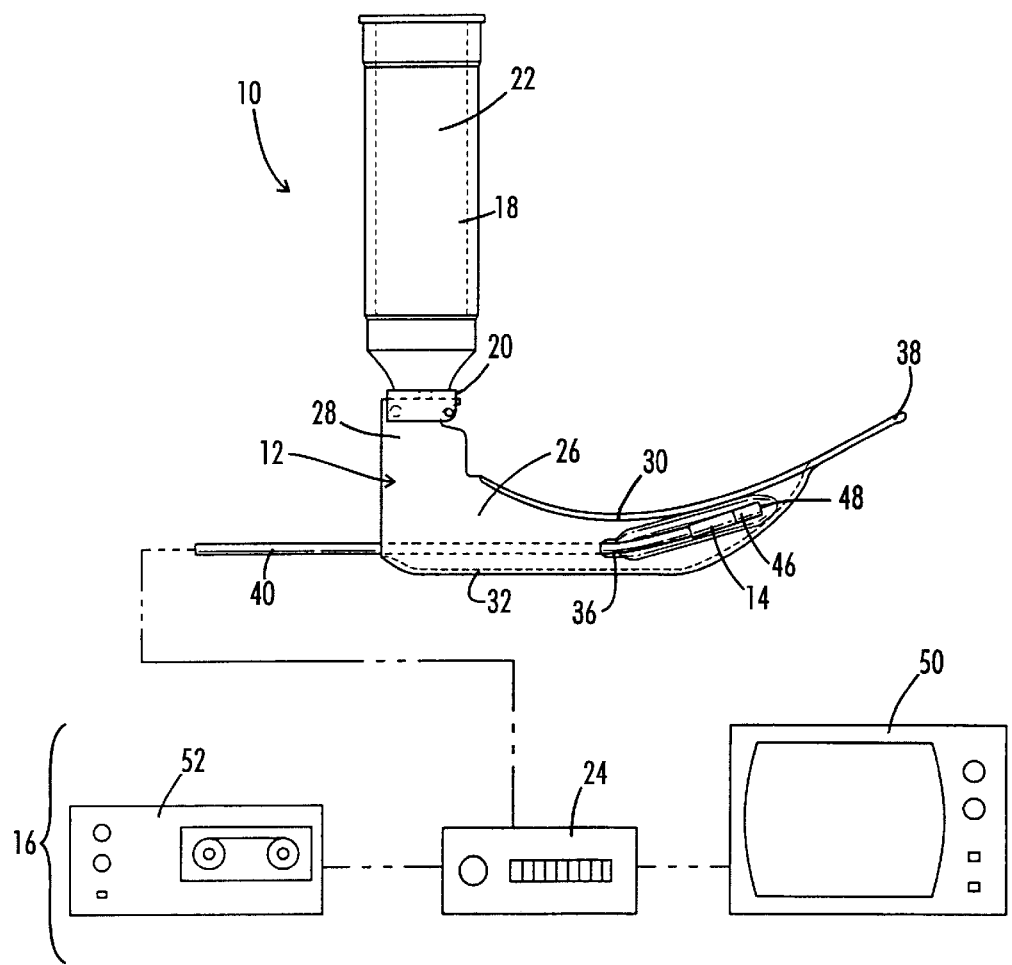
FIG. 1 is a schematic of the laryngoscope blade of the present invention showing a fiberoptic scope mounted to the blade and electrically connected to a remote viewing system.

An embodiment of the present invention is designated generally by the reference numeral 10 in FIG. 1. The present invention comprises a laryngoscope blade 12 having a fiberoptic scope 14 electrically connected to a remote viewing system 16. The laryngoscope blade 12 is operably attached to a handle 18, which includes attachment means or a locking mechanism 20 for attaching the handle 18 to the blade 12.

Figure 2:
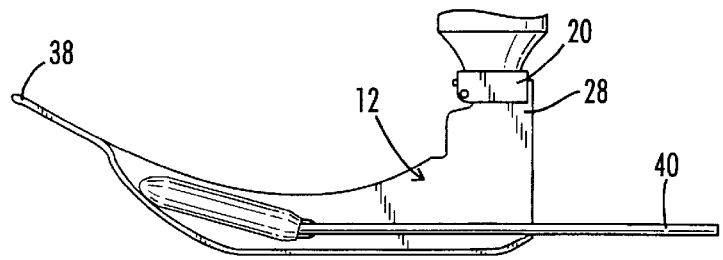
FIG. 2 is an opposite side view of the laryngoscope blade shown in FIG. 1.
Figure 3:
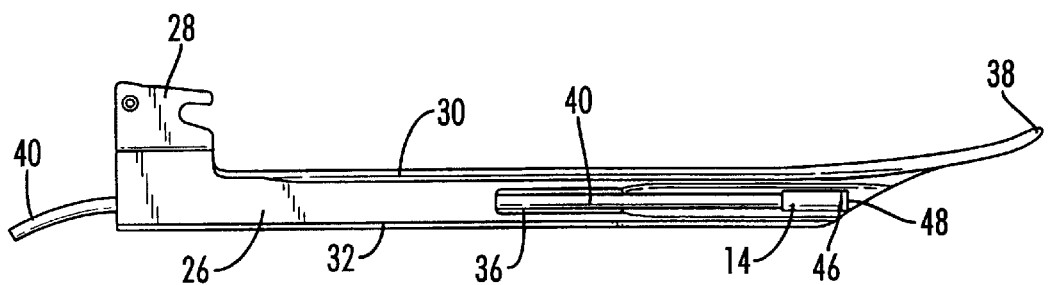
FIG. 3 is a side view of an alternate embodiment of the laryngoscope blade of the present invention.
Figure 4:
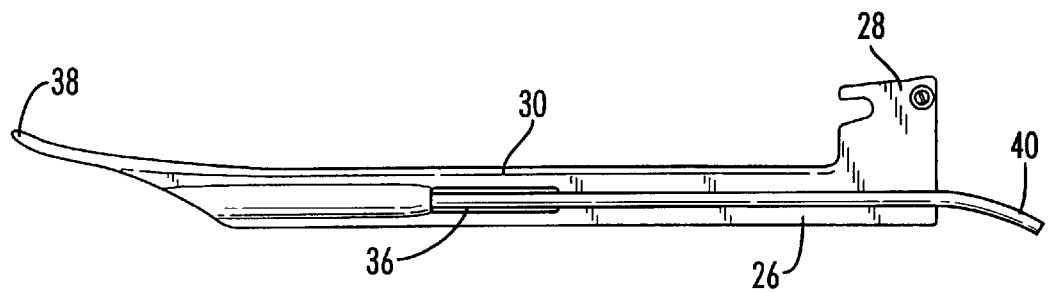
FIG. 4 is an opposite side view of the laryngoscope blade shown in FIG. 3.

With reference to FIGS. 1 and 2, the blade 12 comprises a conventional laryngoscope blade having an elongated plate member 26 extending from a base 28, a flange 30 extending perpendicularly outward from a top edge of the plate member 26, and a lip 32 extending perpendicularly outward from a bottom edge of the plate member 26. The base 28 is configured for cooperative engagement with the attachment mechanism 20 of the handle 18. A slot or opening 36 is formed in the plate member 26 intermediate its ends. At a distal end of the blade 12, the flange 30 preferably extends beyond the end of the plate member 26 and terminates at a rounded blade tip 38. The blade 12 may be either substantially flat, as shown in FIGS. 1 and 2, or curved as shown in FIGS. 3 & 4.

A tubular conduit 40 configured to receive a fiberoptic scope 14 extends along an outer side of the plate member 26, passes through the opening 36 and extends along an inner side of the plate member 26 to a point at the distal end of the blade 12 that will enable the fiberoptic scope 14 housed therein to illuminate the area adjacent the end of the blade 12 and to facilitate viewing of the illuminated area. In some embodiments, the handle 18 contains a hollow cavity 22. This is shown in broken lines in FIG. 1.

The fiberoptic scope 14, which contains fibers for transmitting light to the area adjacent the distal end of the blade 12 and for transmitting visual images to a remote viewing system 16, is housed within the conduit 40. Accordingly, light is transmitted through the fibers to illuminate the area adjacent the end of the blade 12. The fiberoptic scope 14 further includes a camera and lens 46 attached at the distal end of the fibers to enable the transmission of a visual image of the area to the remote viewing system 16.

An optically clear protective cover or cap 48 is provided to protect the lens 46 from secretions and to prevent soiling of the fiberoptic scope 14. The cap 48 is removably attachable to the conduit 40 at the end that extends toward the tip 38 of the blade 12. In the preferred embodiment, the end of the conduit 40 is externally threaded to receive the internally threaded cap 48, thereby enabling the conduit 40 to be reversibly sealed at the end that is inserted into the patient. The cap 48 may be constructed of any suitable material, such as polycarbonate and the like.

The remote viewing system 16 to which the fiberoptic scope 14 is attached includes interfacing equipment 24 for receiving and processing signals from the fiberoptic scope, and for displaying an image. Thus, the remote viewing system 16 comprises a monitor or display 50 for enabling an instructor to simultaneously observe the internal structures of the throat area as a student is inserting the laryngoscope blade 12. A recording device 52 may be provided to enable the recording of the intubation procedures for teaching or instructional purposes. Accordingly, an instructor is able to simultaneously view on the monitor 50 a remote visual image of the area adjacent the tip 38 of the blade 12 as it is being inserted and provide instruction and guidance to a student performing the intubation procedure.

Mode of Operation

Figure 5:
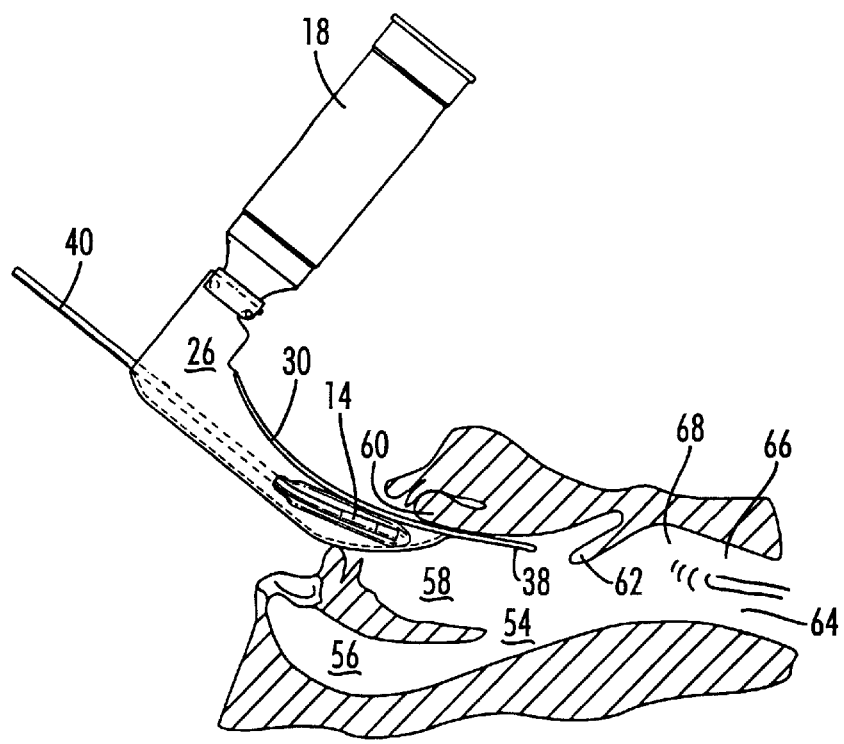
FIG. 5 is a side view showing insertion of the laryngoscope of the present invention into the pharynx of a patient.

With reference to FIG. 5, there is shown a cross-sectional view of the airway and associated anatomical structures of a patient. The pharynx 54 (formed of nasal cavities 56 and the mouth 58), tongue 60, epiglottis 62, esophagus 64, trachea 66 and larynx 68 are shown. A laryngoscope 10 equipped with a fiberoptic scope 14 is shown with the laryngoscope blade 12 inserted into the pharynx 54 of the patient.

Figure 6:
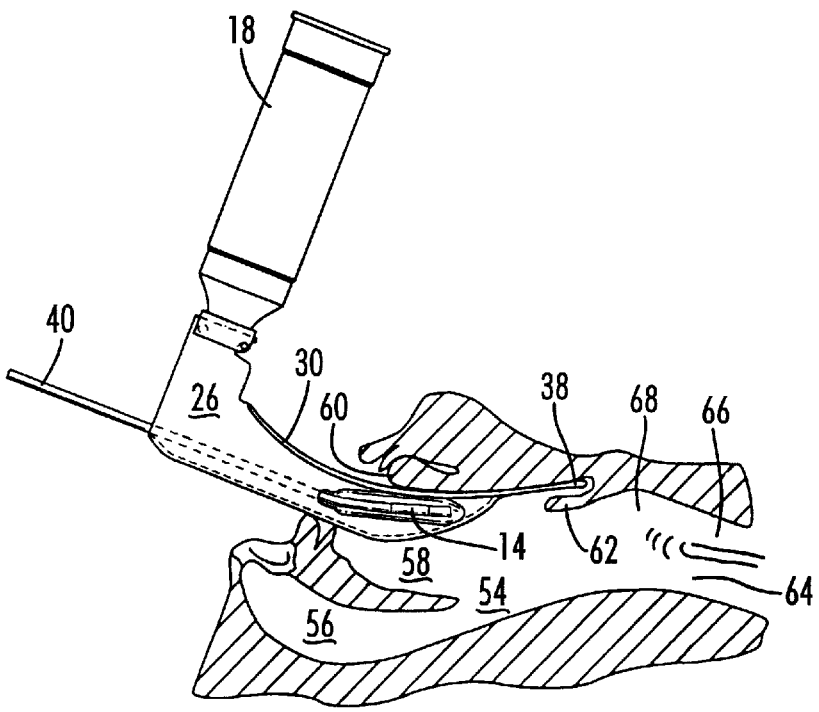
FIG. 6 is a side view showing insertion of the laryngoscope of the present invention into the larynx of a patient.

During insertion of the blade 12, the surrounding anatomical structure is illuminated by the fiberoptic scope 14 and a visual image of the illuminated area is transmitted to a remote monitor 50. In this manner, an instructor can observe the intubation procedure simultaneously as it is being performed by a student. The instructor's view of the anatomy is unobstructed, enabling the instructor to provide instruction and feedback to the student concerning proper positioning of the blade 12. Accordingly, the instructor can direct the student to further insertion of the blade 12 into the larnyx 68 (see FIG. 6).

Thus, although there have been described particular embodiments of the present invention of a new and useful teaching laryngoscope, it is not intended that such references be construed as limitations upon the scope of this invention except as set forth in the following claims.

What is claimed is:

1. A laryngoscope blade to assist in allowing a user to view the larynx of a patient during intubation, comprising:

a blade having a plate portion, a flange portion extending perpendicularly from the plate portion, and a base configured for operative attachment to a handle;

a tubular conduit positioned adjacent the blade for housing a fiberoptic scope, wherein the conduit is adapted to receive and position the fiberoptic scope such that the user's view of the larynx is unobscured; and an optically clear cap removably attached to a distal end of the conduit.

2. The laryngoscope blade of claim 1 wherein a proximal end of the conduit extends beyond a proximal end of the plate portion.

3. A laryngoscope for enabling remote simultaneous observation of an intubation procedure, the laryngoscope comprising:

a blade member configured for attachment to a handle;

a conduit positioned adjacent the blade, the conduit housing an insertable fiberoptic scope therein, the conduit having a curved shape to position the inserted fiberoptic scope so that the remote observation of the intubation procedure is unobscured by the scope; and wherein the fiberoptic scope includes fibers for transmitting light from a light source to an area adjacent the blade and fibers for transmitting a visual image of the illuminated area adjacent the blade to a remote viewing system.

4. The laryngoscope of claim 3, wherein the remote viewing system comprises a monitor for displaying a visual image of the illuminated area adjacent a distal end of the blade.

5. The laryngoscope of claim 3, wherein the remote viewing system comprises a recording device.

6. The laryngoscope of claim 3, further comprising a clear cap removably attached to a distal end of the conduit.

7. A laryngoscope blade to assist in allowing a user to view the larynx of a patient during intubation, comprising:

a blade having a plate portion, a flange portion extending perpendicularly from the plate portion, and a base configured for operative attachment to a handle;

a tubular conduit positioned adjacent the blade for housing a fiberoptic scope, wherein the conduit is adapted to receive and position the fiberoptic scope such that the user's view of the larynx is unobscured; and wherein the plate portion has an inner side, an outer side, and an opening, wherein the conduit extends along the outer-side, passes through the opening, and extends along the inner side.

8. A method for teaching the proper insertion of a laryngoscope blade into the airway of a patient, comprising the steps of:

providing a laryngoscope having a blade member operably attached to a handle and equipped with a conduit containing a fiberoptic scope having illuminating fibers for transmitting light from a light source to an area adjacent a distal end of the blade member and viewing fibers for transmitting a visual image of the illuminated area;

operably connecting the fiberoptic scope to a remote viewing system to enable an instructor to simultaneously observe the airway and associated structures during insertion of the laryngoscope blade and to provide immediate instruction and feedback concerning the proper placement and positioning of the blade member;

inserting the laryngoscope blade into the patient;

observing the airway during the step of inserting; and commenting on the step of inserting.

9. The method of claim 8 further comprising recording the step of inserting the laryngoscope blade.

10. The method of claim 9 further comprising playing a recording of the step of inserting the laryngoscope blade, and wherein the step of commenting on the step of inserting includes commenting on the recording of the step of inserting the laryngoscope blade.

11. The method of claim 8 wherein the step of commenting occurs simultaneously with the step of inserting the laryngoscope blade into the patient.

12. A laryngoscope blade comprising:

a blade having a base adapted to attach to a handle, a plate extending from the blade;

a conduit positioned adjacent to the plate;

a fiberoptic scope inserted into the conduit;

wherein the conduit is curved so as to position the inserted fiberoptic scope out of the field of view of a user of the blade; and wherein the conduit has a proximal end that extends beyond a proximal end of the plate.

13. The laryngoscope blade of claim 12, wherein the plate has an inner side, an outer side, and an opening; and wherein the conduit extends along the inner side, passes through the opening, and extends along the outer side.

* * * * *